United States Patent
Bonner et al.

(10) Patent No.: US 10,426,953 B2
(45) Date of Patent: *Oct. 1, 2019

(54) INTERVENTIONAL MEDICAL SYSTEMS, TOOLS, AND METHODS OF USE

(71) Applicant: Medtronic, Inc., Minneapolis, MN (US)

(72) Inventors: Matthew D Bonner, Plymouth, MN (US); Todd J Sheldon, North Oaks, MN (US); Kathryn Hilpisch, Cottage Grove, MN (US); Noelle C Neafus, Lino Lakes, MN (US); Rónán Wood, Co. na Gallimhe (IE)

(73) Assignee: Medtronic, Inc., Minneapolis, MN (US)

( * ) Notice: Subject to any disclaimer, the term of this patent is extended or adjusted under 35 U.S.C. 154(b) by 244 days.

This patent is subject to a terminal disclaimer.

(21) Appl. No.: 15/400,095

(22) Filed: Jan. 6, 2017

(65) Prior Publication Data

US 2017/0113035 A1    Apr. 27, 2017

Related U.S. Application Data

(63) Continuation of application No. 14/518,087, filed on Oct. 20, 2014, now Pat. No. 9,539,423.
(Continued)

(51) Int. Cl.
*A61N 1/05* (2006.01)
*A61N 1/362* (2006.01)
(Continued)

(52) U.S. Cl.
CPC ........ *A61N 1/0592* (2013.01); *A61B 17/3468* (2013.01); *A61N 1/059* (2013.01);
(Continued)

(58) Field of Classification Search
CPC .............. A61N 1/0592; A61N 1/36507; A61N 1/37205; A61N 1/3624; A61N 1/059;
(Continued)

(56) References Cited

U.S. PATENT DOCUMENTS

| 3,835,864 A | 9/1974 | Rasor et al. |
| 4,471,777 A | 9/1984 | McCorkle, Jr. |

(Continued)

FOREIGN PATENT DOCUMENTS

| EP | 2 614 855 A1 | 7/2013 |
| WO | 2005/118057 A2 | 12/2005 |

(Continued)

OTHER PUBLICATIONS (PCT/US2015/040266) PCT Notification of Transmittal of the International Search Report and the Written Opinion of the International Searching Authority, dated Oct. 8, 2015, 12 pages.
(Continued)

*Primary Examiner* — Phong Son H Dang

(57) ABSTRACT

Delivery tools of interventional medical systems facilitate deployment of relatively compact implantable medical devices that include extensions, for example, cardiac pacing devices that include an extension for atrial sensing, wherein an entirety of the device is contained within the delivery tool while a distal-most portion of the tool is navigated to a target implant site. Once at the implant site, a device fixation member may be exposed out from a distal opening of the tool, for initial deployment, while the extension remains contained within the delivery tool. The tool includes a grasping mechanism, operable, within and without a lumen of the tool, to alternately grip and release the device extension, for example, to position a distal end of the extension after the tool has been withdrawn from over an entirety of the initially deployed device.

14 Claims, 12 Drawing Sheets

Related U.S. Application Data

(60) Provisional application No. 62/025,645, filed on Jul. 17, 2014.

(51) Int. Cl.

| | | |
|---|---|---|
| *A61N 1/365* | (2006.01) | |
| *A61B 17/34* | (2006.01) | |
| *A61N 1/372* | (2006.01) | |
| *A61N 1/375* | (2006.01) | |
| *A61M 25/00* | (2006.01) | |
| *A61B 17/00* | (2006.01) | |
| *A61B 17/22* | (2006.01) | |
| *A61B 17/221* | (2006.01) | |

(52) U.S. Cl.
CPC ....... *A61N 1/3624* (2013.01); *A61N 1/36507* (2013.01); *A61N 1/372* (2013.01); *A61N 1/37205* (2013.01); *A61B 2017/00044* (2013.01); *A61B 2017/00243* (2013.01); *A61B 2017/2215* (2013.01); *A61B 2017/22035* (2013.01); *A61M 25/0026* (2013.01); *A61N 1/3756* (2013.01)

(58) Field of Classification Search
CPC .. A61N 1/372; A61N 1/3756; A61B 17/3468; A61B 2017/00243; A61B 2017/2215; A61B 2017/00044; A61B 2017/22035; A61M 25/0026
See application file for complete search history.

(56) References Cited

U.S. PATENT DOCUMENTS

| | | | | |
|---|---|---|---|---|
| 4,886,065 | A * | 12/1989 | Collins, Jr. | .......... A61B 5/0492 600/377 |
| 7,519,424 | B2 | 4/2009 | Dennis et al. | |
| 8,504,156 | B2 * | 8/2013 | Bonner | ................ A61N 1/3756 607/36 |
| 8,527,068 | B2 | 9/2013 | Ostroff | |
| 8,634,912 | B2 * | 1/2014 | Bornzin | ............... A61N 1/3756 607/119 |
| 8,634,919 | B1 | 1/2014 | Hou et al. | |
| 8,670,842 | B1 * | 3/2014 | Bornzin | ................. A61N 1/375 607/125 |
| 9,283,382 | B2 * | 3/2016 | Berthiaume | ......... A61N 1/0587 |
| 9,446,248 | B2 | 9/2016 | Sheldon et al. | |
| 9,526,522 | B2 | 12/2016 | Wood et al. | |
| 9,539,423 | B2 | 1/2017 | Bonner et al. | |
| 10,111,686 | B2 * | 10/2018 | Bartosch | .............. A61N 1/0587 |
| 2006/0085041 | A1 * | 4/2006 | Hastings | ............... A61N 1/0587 607/33 |
| 2010/0198288 | A1 * | 8/2010 | Ostroff | ................. A61N 1/0573 607/9 |
| 2012/0109149 | A1 * | 5/2012 | Bonner | .................. A61N 1/057 606/129 |
| 2012/0172891 | A1 * | 7/2012 | Lee | ..................... A61B 17/3468 606/129 |
| 2012/0172892 | A1 * | 7/2012 | Grubac | ................ A61N 1/3756 606/129 |
| 2013/0023975 | A1 | 1/2013 | Locsin | |
| 2013/0035748 | A1 * | 2/2013 | Bonner | .................. A61N 1/056 623/1.11 |
| 2013/0079798 | A1 * | 3/2013 | Tran | .................... A61N 1/37205 606/129 |
| 2013/0103047 | A1 * | 4/2013 | Steingisser | .......... A61N 1/3756 606/129 |
| 2013/0110219 | A1 * | 5/2013 | Bornzin | ............... A61N 1/3756 607/127 |
| 2013/0116740 | A1 * | 5/2013 | Bornzin | ............... A61N 1/3756 607/9 |
| 2013/0131693 | A1 * | 5/2013 | Berthiaume | ......... A61N 1/3756 606/129 |
| 2014/0107723 | A1 * | 4/2014 | Hou | ...................... A61N 1/362 607/28 |
| 2015/0051610 | A1 * | 2/2015 | Schmidt | ............. A61N 1/37205 606/129 |
| 2015/0094668 | A1 * | 4/2015 | Wood | ................ A61M 25/0105 604/256 |
| 2016/0015322 | A1 | 1/2016 | Anderson et al. | |

FOREIGN PATENT DOCUMENTS

| | | |
|---|---|---|
| WO | 2013/032624 A2 | 3/2013 |
| WO | 2013/074780 A1 | 5/2013 |

OTHER PUBLICATIONS (PCT/US2015/040260) PCT Notification of Transmittal of the International Search Report and the Written Opinion of the International Searching Authority, dated Nov. 9, 2015, 11 pages.

Prosecution History from U.S. Appl. No. 14/518,087, dated Oct. 20, 2014 through Sep. 30, 2016, 15 pp.

* cited by examiner

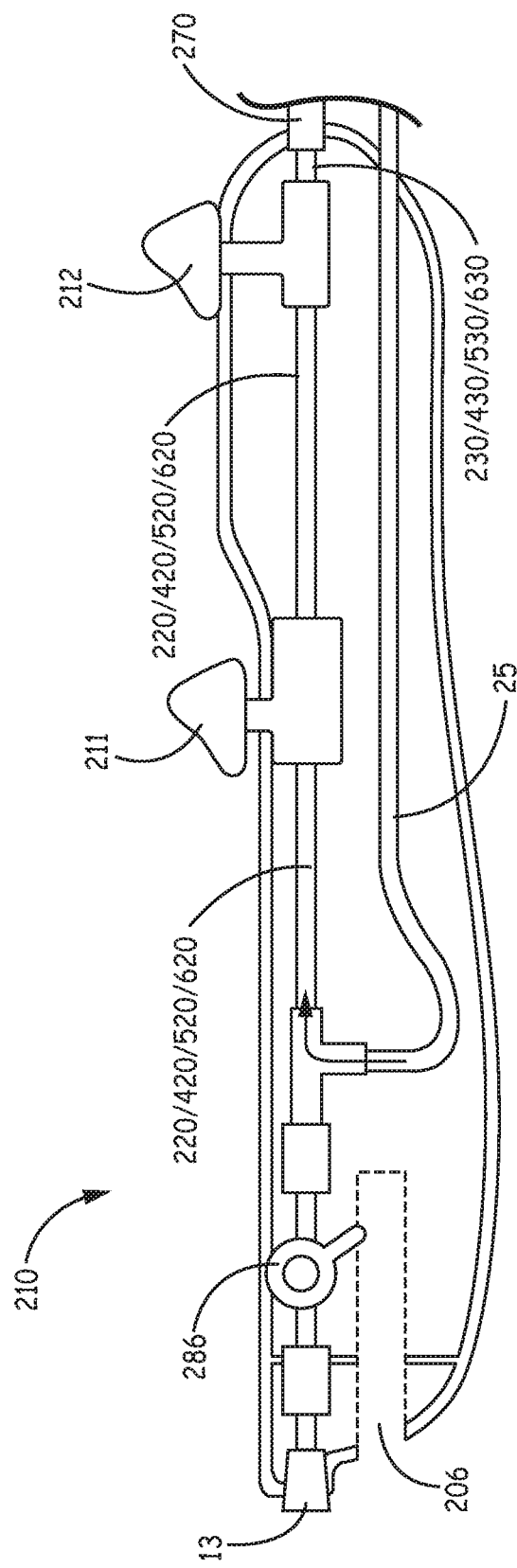

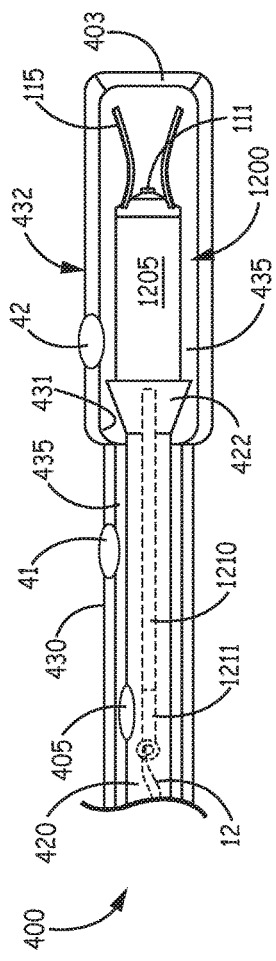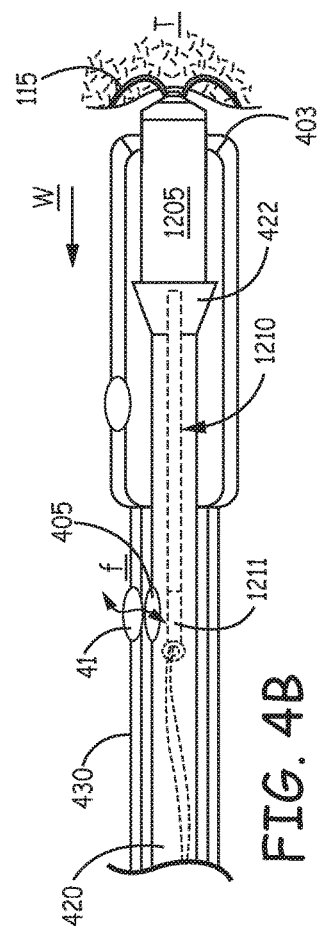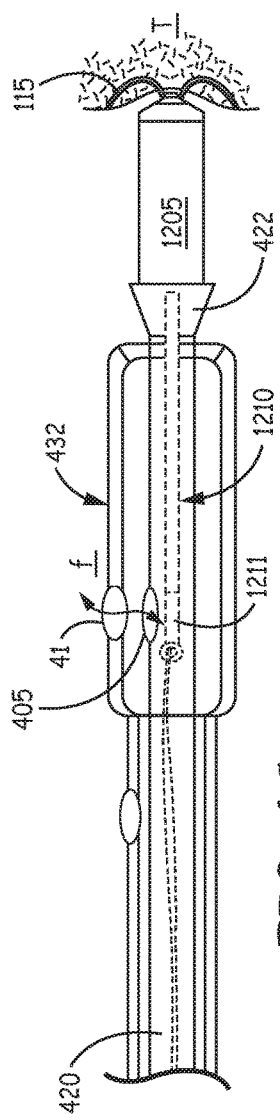

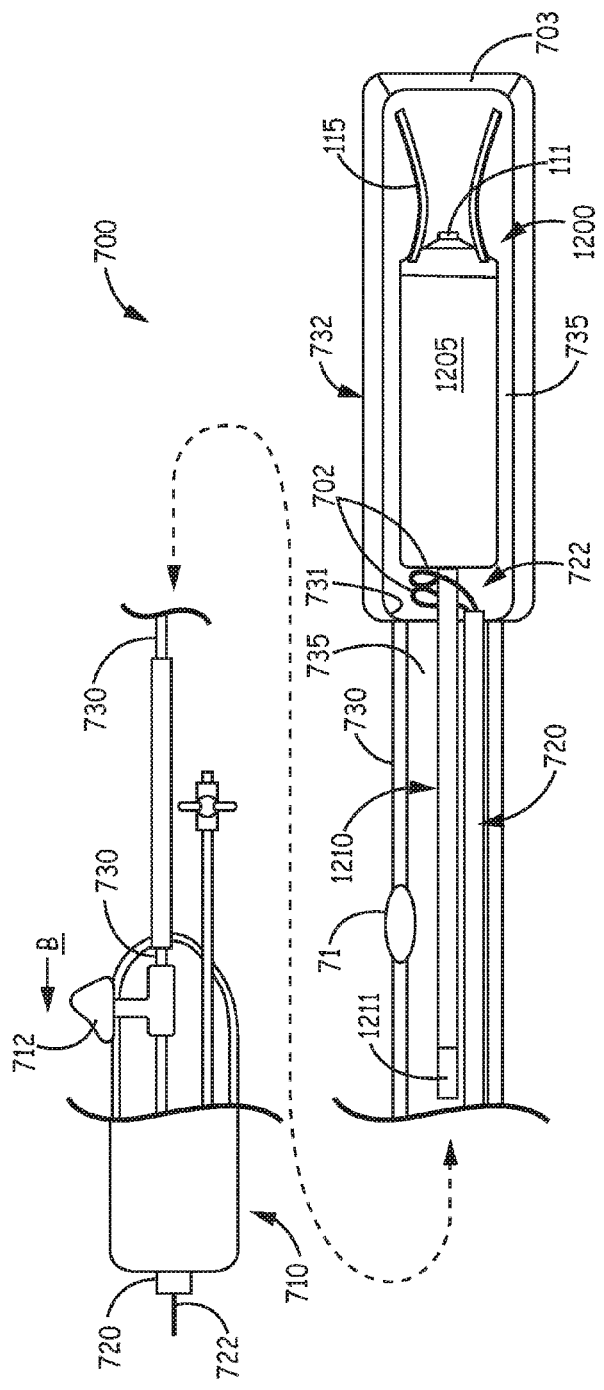
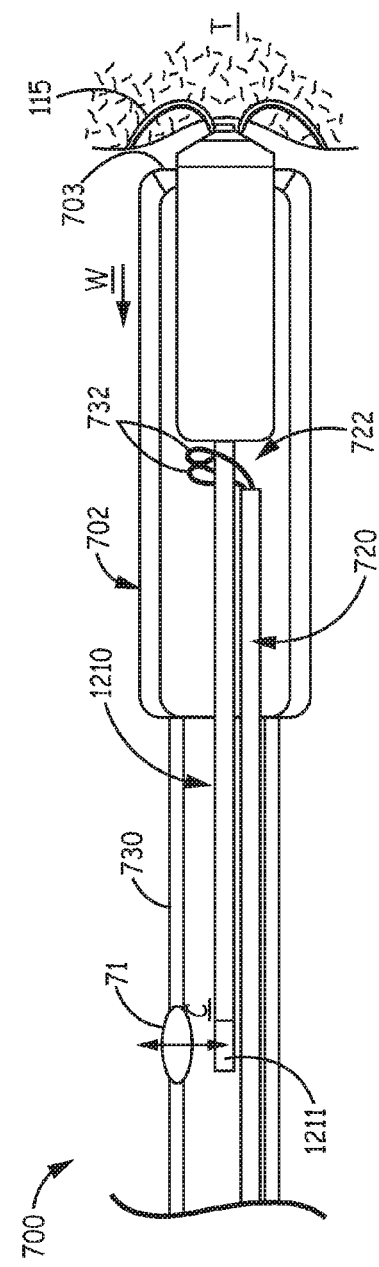
FIG. 7A
FIG. 7B

INTERVENTIONAL MEDICAL SYSTEMS, TOOLS, AND METHODS OF USE

CROSS-REFERENCE TO RELATED APPLICATION

This application is a continuation of U.S. patent application Ser. No. 14/518,087 (now allowed), filed Oct. 20, 2014 and entitled "INTERVENTIONAL MEDICAL SYSTEMS, TOOLS AND METHODS OF USE", which issued as U.S. Pat. No. 9,539,423, and which claims priority to United States Provisional Patent Application Ser. No. 62/025,645, which was filed on Jul. 17, 2014, both of which are hereby incorporated by reference in their entirety. The present application also includes subject matter that is similar to U.S. patent application Ser. No. 14/518,128 filed Oct. 20, 2014 and now issued as U.S. Pat. No. 9,446,248, and which is incorporated by reference in its entirety.

FIELD OF THE DISCLOSURE

The present invention pertains to interventional medical systems, and more particularly to tools and associated methods configured to facilitate percutaneous transvenous deployment of relatively compact implantable medical devices.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, like a device 100, which is shown in FIG. 1, implanted within the right ventricle RV of the heart. FIG. 1 illustrates device 100 having been deployed out from a distal portion of a standard guiding catheter 150, which has been maneuvered up through the inferior vena cava IVC and into the right ventricle RV from the right atrium RA, according to methods known in the art of interventional cardiology. With further reference to FIG. 1, an hermetically sealed housing 105, preferably formed from a biocompatible and biostable metal such as titanium, contains a pulse generator, or an electronic controller (not shown), to which an electrode 111 is coupled, for example, by a hermetic feedthrough assembly (not shown) like those known to those skilled in the art of implantable medical devices. FIG. 1 further illustrates device 100 including a fixation member 115, which engages tissue at the implant site to secure device 100 thereto so that electrode 111 is held in intimate contact with the tissue at the site. Housing 105 may be overlaid with an insulative layer, for example, medical grade polyurethane, parylene, or silicone, and a portion of housing 105 from which the insulative layer is removed, may be employed as another electrode to function in conjunction with electrode 111 for ventricular bipolar pacing and sensing.

SUMMARY

Delivery tools of interventional medical systems disclosed herein facilitate deployment of relatively compact implantable medical devices that include extensions, for example, a cardiac pacing device that includes an extension for atrial sensing, or that includes an extension for atrial pacing and sensing. According to embodiments and methods of the present invention, an entirety of such a device is contained within a delivery tool, while a distal-most portion of the tool is navigated to a target implant site within a patient's venous system; the tool is configured to expose, out from a distal opening thereof, a fixation member of the device for initial deployment at the site, wherein a grasping mechanism of the tool, which is configured to grip the device extension within the distal-most portion of the tool, may be used to apply a tug force to the device after the fixation member is engaged, for example, to test a holding force of the fixation member or to disengage the fixation member. The grasping mechanism, according to some embodiments, includes a tubular shaft and a pair of arms longitudinally moveable within a lumen of the shaft, wherein a curved distal end of each arm protrudes out from a distal opening of the lumen of the shaft; longitudinal movement of the arms within the lumen of the shaft spreads the arms apart from one another or closes the arms together. According to some methods, after an operator engages fixation member with the tissue, the operator may manipulate the grasping mechanism to position a distal end of the extension at a desired location, for example, in a right atrium.

In some embodiments, the delivery tool further includes a conductive feature located proximal to, and in proximity to the distal-most portion thereof, which provides a conductive pathway between the sense electrode of the aforementioned device extension and a location outside the tool (e.g. the patient's venous blood pool). Thus, according to some methods, the operator can evaluate sensing, via the sense electrode of the extension of the device, while the extension is still contained within the delivery tool. According to some embodiments, the conductive feature forms the conductive pathway by providing fluid communication between the sense electrode of the extension and the location outside the deployment tube; alternately the conductive feature is formed by an electrically conductive segment integrated into the wall of the tool that makes electrical contact with the sense electrode, either directly or indirectly.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 3B is a longitudinal cross-section view through a handle of the tool of FIG. 3A, according to some embodiments;

FIGS. 4A-C are partial cut-way section views of a distal portion of an interventional medical system that includes a delivery tool, like the tool of FIGS. 3A-B, according to some embodiments and methods;

FIGS. 7A-B are partial cut-way section views of proximal and distal portions of an interventional medical system that includes a delivery tool, according to some additional embodiments.

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
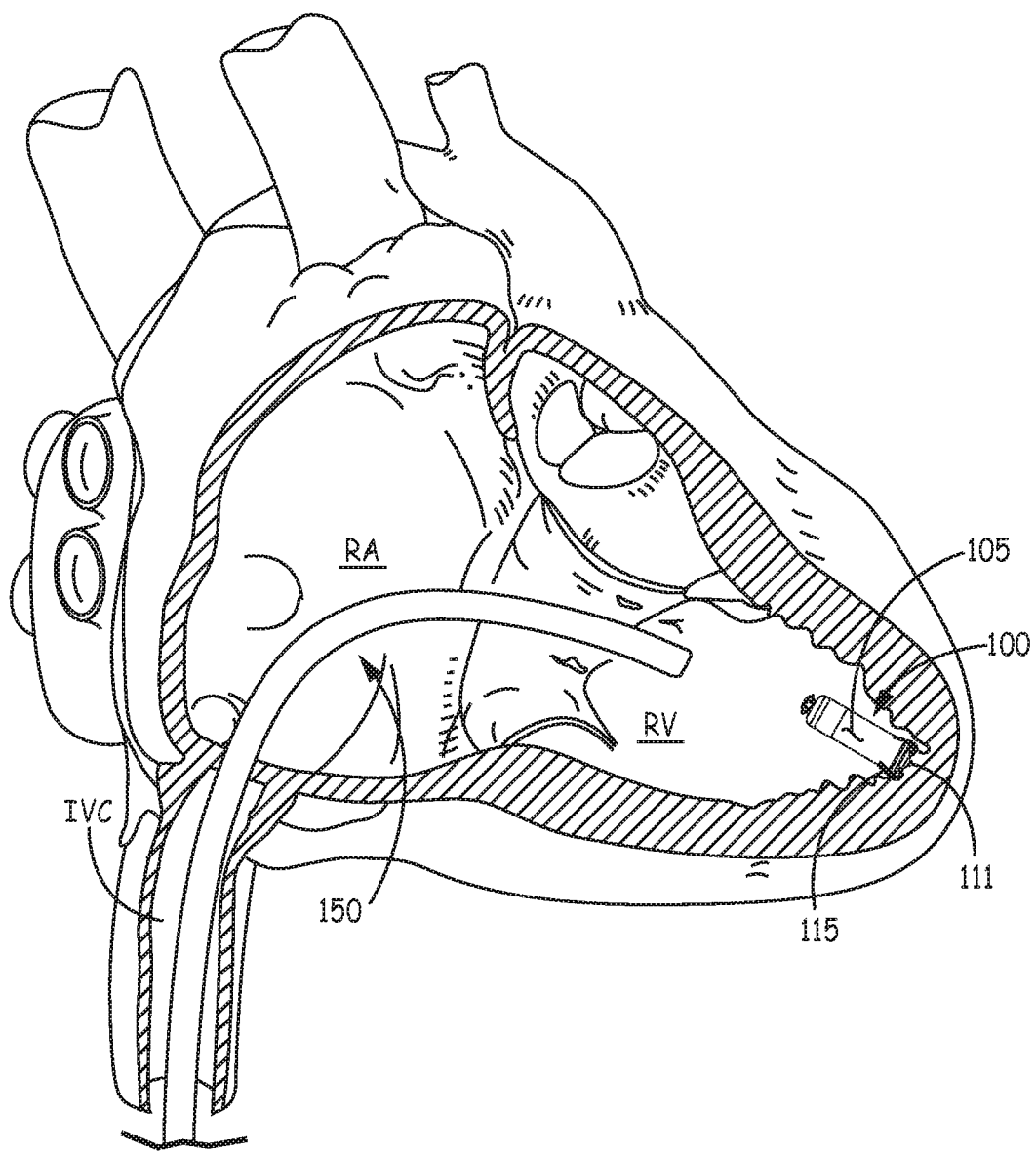
FIG. 1 is a schematic showing an exemplary interventional medical system for cardiac stimulation.
Figure 2A:
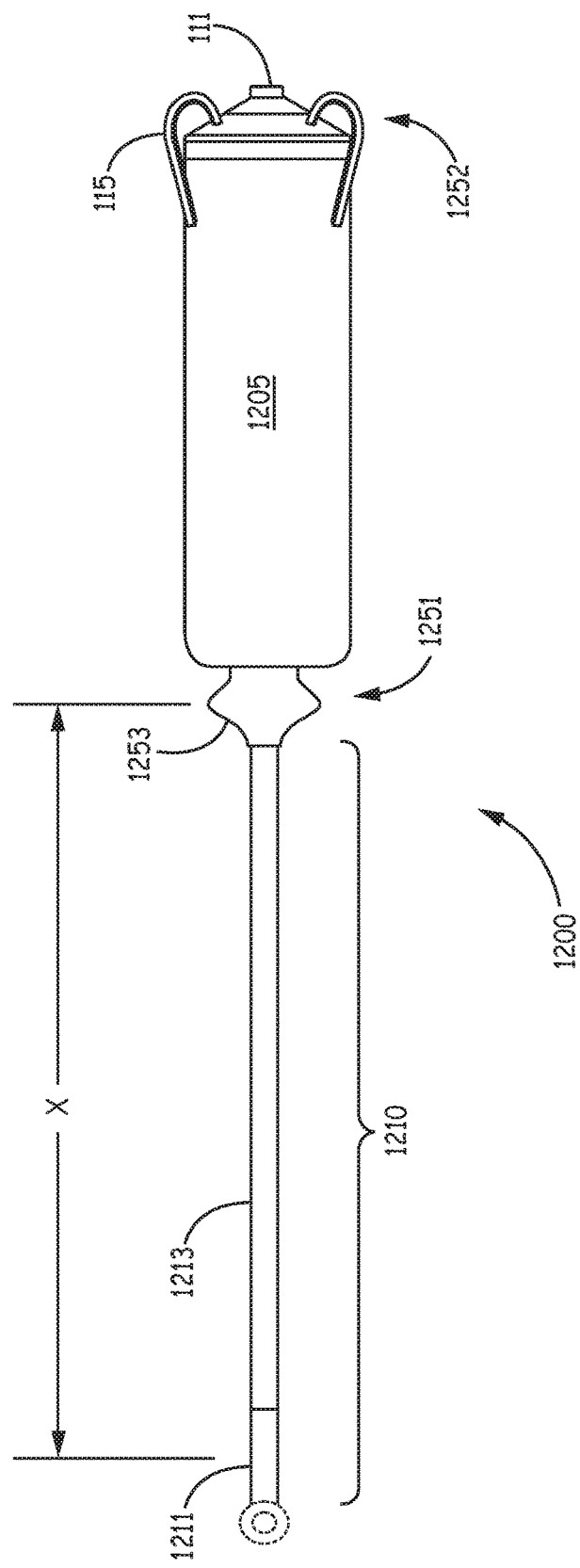
FIG. 2A is a plan view of an exemplary implantable medical device, which may be employed by systems of the present invention.
Figure 2B:
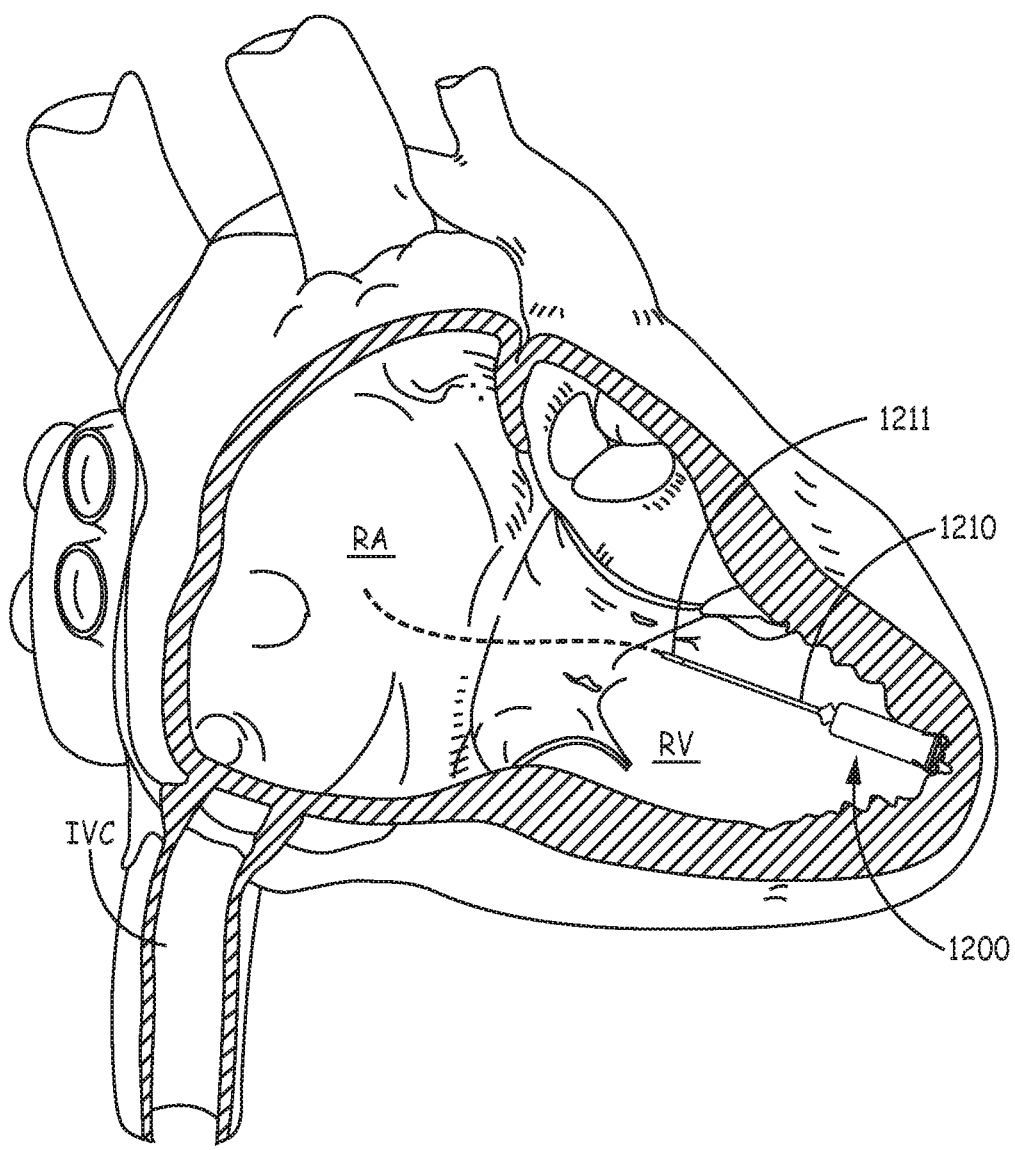
FIG. 2B is a schematic showing the exemplary device of FIG. 2A implanted in a right ventricle.

FIG. 2A is a plan view of an exemplary implantable medical device 1200, which may be employed in systems of the present invention, for example, those described below in conjunction with FIGS. 3-8. FIG. 2A illustrates device 1200 including a hermetically sealed housing 1205, cardiac pacing and sensing electrodes 111, 1211, and fixation member 115 coupled to a distal end 1252 of device housing 1205. Like the above described housing 105 of device 100 (FIG. 1), housing 1205 of device 1200 contains a power source and an electronic controller (not shown) within a relatively compact form factor, wherein electrode 111 is coupled to the controller via a hermetically sealed feedthrough assembly known in the art. Fixation member 115, like in device 100, holds electrode 111 in intimate contact with tissue at an implant site, for example, as illustrated in FIG. 2B. With further reference to FIG. 2A, unlike device 100, device 1200 includes an extension 1210 on which sense electrode 1211 is mounted.

Extension 1210 extends proximally from a proximal end 1251 of device housing 1205, such that sense electrode 1211 is spaced a distance X from proximal end 1251 of housing 1205. The distance X locates sense electrode 1211 for atrial sensing (P-waves), when device 1200 is implanted in the right ventricle RV, for example, as shown in FIG. 2B. The distance X may be between approximately 6 cm and approximately 10 cm, such that electrode 1211 is located in the right ventricle RV, as shown; or, according to alternate embodiments, distance X may be between approximately 10 cm and approximately 15 cm, such that electrode is located in the right atrium RA, for example, as indicated with the dashed line in FIG. 2B. According to the illustrated embodiment, extension 1210 includes an insulated conductor 1213, for example, a coiled medical grade stainless steel or MP35N wire disposed within a medical grade silicone or polyurethane jacket, which is electrically coupled to device housing 1205, for example, via a crimp or a weld.

Figure 3A:
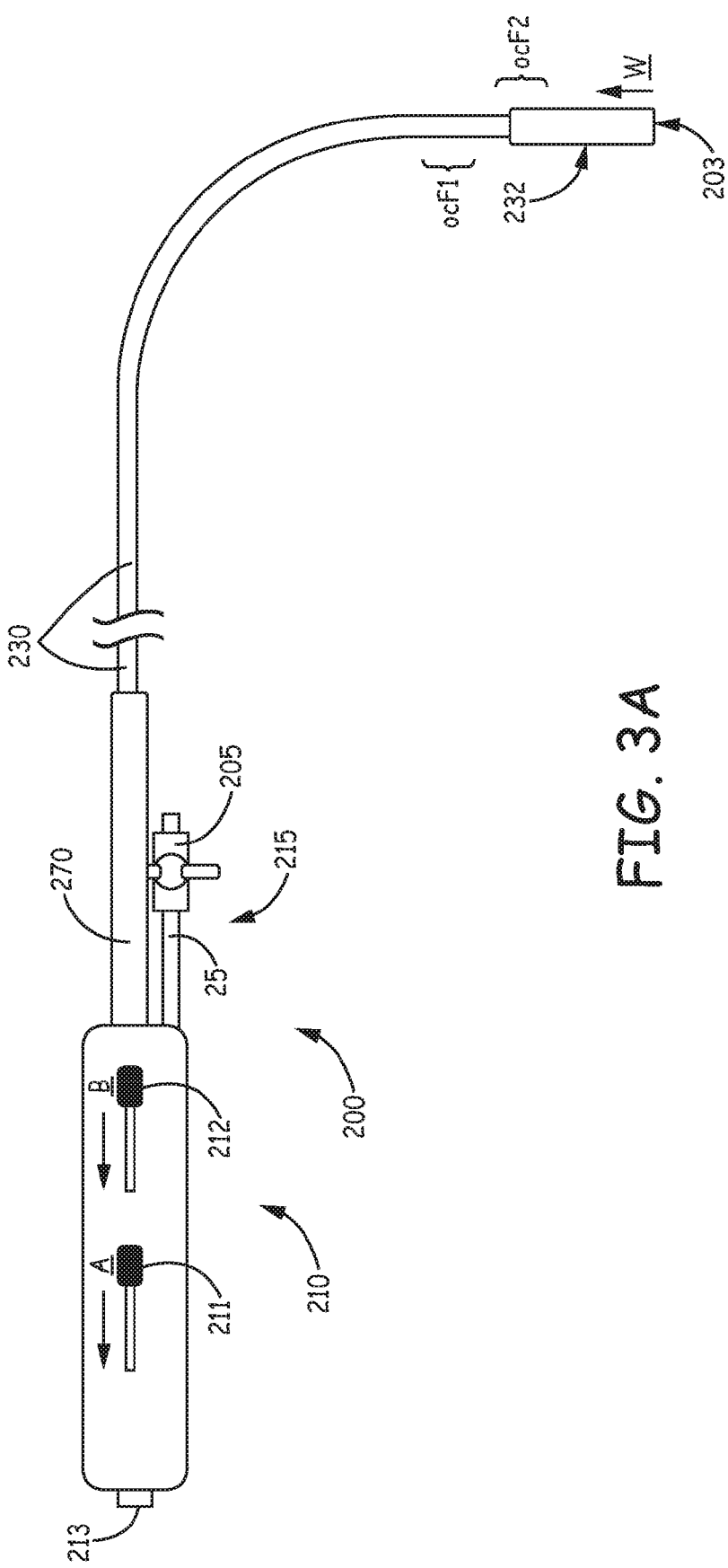
FIG. 3A is a plan view of a delivery tool, according to some embodiments of the present invention.

FIG. 3A is a plan view of a delivery tool 200 that may be included together with device 1200 in an interventional medical system, according to some embodiments. FIG. 3A illustrates tool 200 including a handle 210, and an outer assembly, which is formed by an elongate deployment tube 230 and an outer, stabilizing sheath 270 that surrounds a proximal portion of deployment tube 230 in proximity to handle 210. FIG. 3B is a longitudinal cross-section view through handle 210, in which a proximal end of sheath 270 is shown secured to handle 210, and a proximal end of deployment tube 230 is shown coupled to a control member 212 of handle 210 such that tube 230 is moveable, via control member 212, relative to sheath 270, according to some embodiments. With further reference to FIG. 3B, tool 200 also includes an elongate inner member 220, which extends within a lumen of deployment tube 230 such that an entirety of deployment tube 230 is also movable with respect to the inner member 220, via control member 212. Inner member 220 includes a distal end (not shown), which is located within a distal-most portion 232 of deployment tube 230 and is configured to engage an implantable medical device by abutting an end of the device, for example, proximal end 1251 of device 1200. FIGS. 3A-B further illustrate tool 200 including a flushing subassembly 215 coupled to handle 210, wherein subassembly 215 includes a tube 25 defining a flush lumen, which extends between a connector port 205 (e.g., a stopcock type fitting) and one or more lumens of inner member 220. The arrow in FIG. 3B indicates the flow of a flushing fluid (e.g., saline) from the flush lumen to the one or more lumens of inner member 220, and, although not shown, inner member 220 may include one or more ports formed in the sidewall thereof to allow the flushing fluid to flow through the lumen of deployment tube as well.

With further reference to FIG. 3A, the lumen of deployment tube 230, along a length of distal-most portion 232, is sized to contain the distal end of inner member 220 along with the entirety of device housing 1205; and a lumen (not shown) of inner member 220, which extends proximally from an opening terminating the distal end of inner member 220, is sized to accommodate extension 1210 of device 1200, when the distal end of inner member 220 abuts proximal end 1251 of device housing 1205. Thus a distal portion of tool 200, with an entirety of device 1200 contained therein, may be navigated to a target implant site, for example, in the right ventricle RV by advancing tool 200 through a venous system of the patient, for example, from a femoral venous access site and up through the inferior vena cava IVC (FIG. 2B). A length of deployment tube 230, between handle assembly 210 and distal opening 203 of deployment tube 230, when tube 230 is in the position shown in FIG. 3A, may be between approximately 103 cm and approximately 107 cm, for example, to reach the right ventricle RV from the femoral access site. According to some embodiments of the present invention, delivery tool 200 includes articulating features to facilitate the navigation of the distal portion of delivery tool 200 to the target implant site; for example, inner member 220 of delivery tool 200 may include a pull wire (not shown) integrated therein and coupled to another control member 211 of handle 210 that, when moved per arrow A, causes inner member 220 and deployment tube 230 to bend along distal portions thereof. Suitable construction detail for a delivery tool like tool 200 is described in co-pending and commonly assigned U.S. patent application Ser. No. 14/039,937, the description of which is hereby incorporated by reference.

Once tool 200 is located so that a distal opening 203 (FIG. 3A) of the lumen of deployment tube 230 is located adjacent to the implant site, control member 212 may be moved, per arrow B, to withdraw deployment tube 230, per arrow W, and expose fixation member 115 (FIG. 2A) of device 1200 for engagement with tissue at the target site. When fixation member 115 is engaged such that electrode 111 is in intimate contact with the tissue, pacing and sensing performance of device 1200 may be evaluated without having to withdraw delivery tool 200 proximally from device 1200 to expose a remainder of device 1200, because, according to embodiments of the present invention, tool 200 includes conductive features for creating a conductive pathway between sense electrode 1211 of device extension 1210 and a location outside tool 200 (e.g., the blood pool of the patient's venous system), while extension 1210 is still contained within inner member 220 and deployment tube 230. FIG. 3A illustrates potential locations of one or more outer conductive features ocF1, ocF2 of deployment tube 230, which work in conjunction with inner conductive features of inner member 220 to create the conductive pathway, according to various embodiments described below.

FIGS. 4A-C are partial cut-way section views of a distal portion of an interventional medical system that includes a delivery tool 400, which is similar, in some respects, to delivery tool 200, according to some embodiments and methods of the present invention. FIGS. 4A-C illustrate tool 400 including an inner member 420 and a deployment tube 430, wherein inner member 420 extends within a lumen 435 of tube 430 such that tube 430 is movable with respect to inner member 420, for example, via a control member of a handle of tool 400, for example, control member 212 of handle 210 (FIG. 3B). FIG. 4A shows and entirety of device 1200 contained within the distal portion of tool 400, with device housing 1205, electrode 111, and fixation member 115 all located in a distal-most portion 432 of deployment tube 430, and with housing 1205 abutting a distal end 422 of inner member 420 so that extension 1210 of device 1200 (shown with dashed lines) extends within a lumen of inner member 420. According to an exemplary embodiment, distal-most portion 432 has a length of approximately 3.5 cm (~1.4 inch), an inner diameter of approximately 0.275 inch (~0.7 cm), and an outer diameter of approximately 0.3 inch (~0.8 cm). Distal end 422 of inner member 420 is shown being enlarged relative to a remainder of inner member 420 and thus constrained from moving proximally out of distal-most portion 432 by a shoulder 431 of distal-most portion 432, according to some embodiments. Although not shown, it should be understood that the lumen of inner member 420 extends proximally from an opening thereof that terminates distal end 422 of inner member 420, and, according to an exemplary embodiment, the lumen of inner member 420 has a diameter between approximately 1.8 mm (0.070 inch) and approximately 2.4 mm (0.095 inch), to accommodate extension 1210 extending therein. According to some embodiments, the lumen of inner member 420 extends to a proximal end of inner member 420, for example, which is located within handle 210 of tool 400; according to some alternate embodiments, inner member 420 includes a multi-lumen length extending from the proximal end of inner member 420 to the above-described portion of the lumen that accommodates device extension 1210.

FIGS. 4A-C further illustrate deployment tube 430 including outer conductive features 41, 42, and inner member 420 including an inner conductive feature 405, wherein conductive features 41, 42, 405 are defined by apertures formed through a wall of deployment tube 430 and a wall of inner member 420, respectively. According to the illustrated embodiment, inner conductive feature 405 is located to provide a conductive pathway, via fluid communication, between sense electrode 1211 of device extension 1210 and one of outer conductive features 41, 42 of deployment tube 430, when aligned therewith, as shown in FIG. 4B or FIG. 4C. With reference to FIG. 4B, when an operator initially retracts/withdraws deployment tube 430, per arrow W, to expose fixation member 115 out through a distal opening 403 of lumen 435 of tube 430, and has pushed inner member 420 to engage fixation member 115 with tissue T at an implant site, outer conductive feature 41, which is located proximal to distal-most portion 432 of tube 430, is aligned with inner conductive feature 405 to allow fluid communication, per arrow f, between the blood pool outside deployment tube 430 and sense electrode 1211. A saline flush, for example, injected at connector port 205 (described above in conjunction with FIGS. 3A-B), through the lumen of inner member 420, and through features 41, 405 can create a conductive pathway, per double-headed arrow f, which allows the operator to evaluate sensing via sense electrode 1211, for example, the sensing of atrial activity (e.g., P-waves) when the implant site is in the right ventricle RV. With reference to FIG. 4C, when the operator retracts deployment tube 430 farther, so that distal end 422 of inner member 420 and device housing 1205 are both exposed outside tool 400, outer conductive feature 42, which is located along distal-most portion 432 of tube 430, is aligned with inner conductive feature 405 to also allow fluid communication that creates the conductive pathway, per arrow f, thereby allowing the aforementioned sensing evaluation. In the absence of the aforementioned saline flush, blood flow into lumen 435 of deployment tube 430, through one or both of features 41, 42, and then into the lumen of inner member 420, through feature 405, can create a sufficient conductive pathway. Each conductive feature 41, 42, 405 may include a single aperture or a plurality of apertures, for example, formed about a perimeter of the respective wall. Although FIGS. 4A-C illustrate deployment tube 430 including two outer conductive features 41, 42, according to some alternate embodiments, deployment tube 430 includes only one of outer conductive features 41, 42.

Figure 5A:
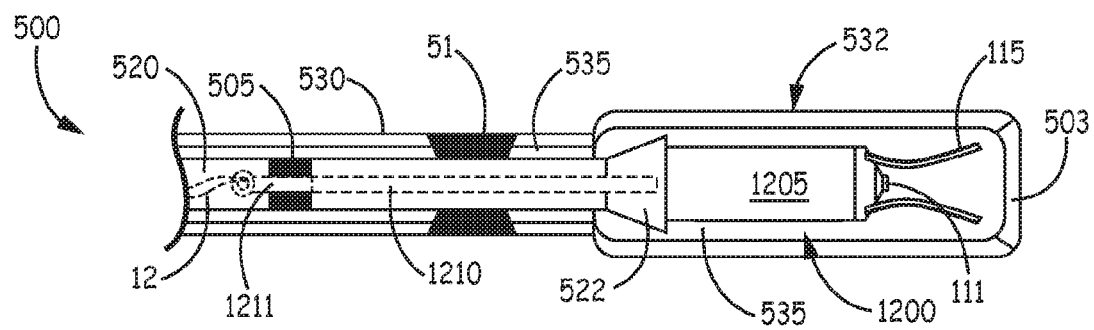
FIGS. 5A-B are partial cut-way section views of a distal portion of an interventional medical system that includes a delivery tool, like the tool of FIGS. 3A-B, according to some alternate embodiments and methods.
Figure 5B:
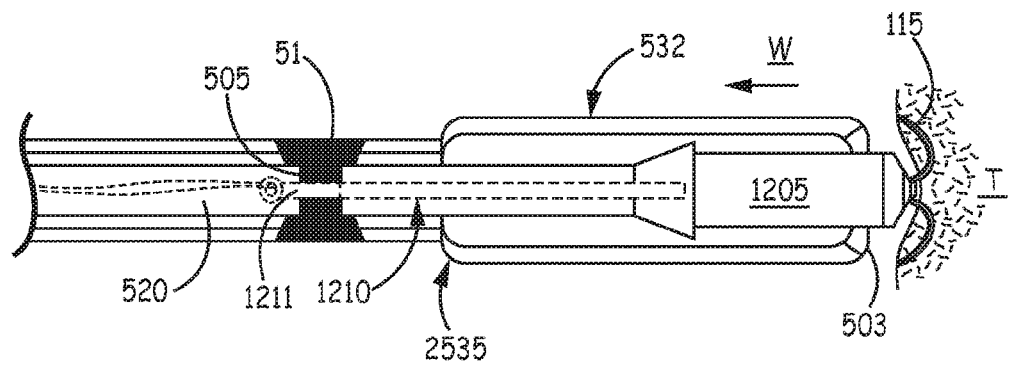

FIGS. 5A-B are partial cut-way section views of a distal portion of an interventional medical system that includes a delivery tool 500, according to some alternate embodiments and methods. Like delivery tool 400, FIG. 5A illustrates tool 500 including an inner member 520 and a deployment tube 530, wherein inner member 520 extends within a lumen 535 of tube 530 such that tube 530 is movable with respect to inner member 520, for example, via a control member of a handle of tool 500, for example, control member 212 of handle 210 (FIG. 3B). Also like tool 400, FIG. 5A shows device 1200 contained in a distal-most portion 532 of tube 530 with device housing 1205 abutting a distal end 522 of inner member 520, and with device extension 1210, again shown with dashed lines, extending within a lumen of inner member 520, wherein the lumen is similar to that of inner member 420 described above. FIGS. 5A-B further illustrate deployment tube 530 including an outer conductive feature 51, and inner member 520 including an inner conductive feature 505, wherein conductive features 51, 505 are defined by electrically conductive segments of a wall of deployment tube 530 and a wall of inner member 520, respectively. According to the illustrated embodiment, when extension 1210 extends within the lumen of inner member 520, as shown, electrode 1211 of extension 1210 may interface with inner conductive feature 505 to make electrical contact therewith; and, with reference to FIG. 5B, when an operator initially retracts/withdraws deployment tube 530, per arrow W, to expose device fixation member 115 out through a distal opening 503 of lumen 535 of tube 530, and has pushed inner member 520 to engage fixation member 115 with tissue T at an implant site, outer conductive feature 51, for example, located proximal to distal-most portion 532 of tube 530, is aligned with inner conductive feature 505 to make electrical contact therewith. An outer surface of outer conductive feature 51 is in conductive contact with the blood pool outside tool 500, so that the aligned conductive features 51, 505, for example, as illustrated in FIG. 5B, provide a conductive pathway between the interfacing sense electrode 1211 and the blood pool, which allows the operator to evaluate sensing via sense electrode 1211, for example, the sensing of atrial activity (e.g., P-waves) as described above, without having to withdraw tool 500 from over an entirety of device 1200.

The interfaces between sense electrode 1211 and inner conductive feature 505 and between inner conductive feature 505 and outer conductive feature 51 may be ones of direct electrical contact, or simply through conductors where direct contact is not required; in either case features 505, 51 provide the conductive pathway between sense electrode 1211 and the blood pool outside tube 530. The electrically conductive segments of inner and outer conductive features 505, 51, according to some embodiments, are formed by an electrically conductive material dispersed within the walls of inner member 520 and deployment tube 530, for example, being in the form of a woven braid of conductive strands, such as fine stainless steel wire, integrated into the walls, wherein, a bulk of each wall may be formed from a polyether block amide. According to some alternate embodiments, the electrically conductive segments of inner and outer conductive features 505, 51 are formed by conductive inserts joined to the walls of inner member 520 and deployment tube 530, for example, stainless steel rings.

With reference back to FIGS. 2A-B, inner conductive feature 405, 505 of each tool 400, 500 is located relative to distal end 422, 522 of the corresponding inner member 420, 520 to either accommodate a length of extension 1210 in which distance X is between approximately 6 cm and approximately 10 cm, such that electrode 1211 is located in the right ventricle RV, or to accommodate a longer length of extension 1210 in which distance X is between approximately 10 cm and approximately 15 cm, such that electrode 1211 is located in the right atrium RA.

For any of the above-described embodiments, if the operator finds that the sensing is adequate, after the operator has retracted deployment tube 430, 530 relative to inner member 420, 520 and device 1200, engaged fixation member 115 of device 1200 at the target implant site in the right ventricle RV, and evaluated atrial sensing via the conductive pathway formed by the corresponding inner and outer conductive features, the operator may withdraw tool 400, 500 from over an entirety of the implanted device 1200. With further reference to FIG. 2A, an optional eyelet feature terminating a proximal end of extension 1210 is shown with dashed lines. The optional eyelet feature is useful for attaching a tether 12 (shown with dashed lines in FIGS. 4A and 5A) to device 1200, while the device is loaded in tool 400, 500 and during the deployment of device 1200 out from tool 400, 500. With reference to FIG. 3B, tether 12 may extend within the lumen of inner member 420, 520 and out from a proximal opening 13 thereof, so that the operator may have access to the tether in proximity to handle 210. With further reference to FIG. 3B, a proximal end of tether 12 may be attached to a holder (not shown) that fits within a receptacle 206 of handle 210, and a valve member 286 of handle 210 (e.g., a stopcock type valve) may be configured to alternately secure and release tether 12 within the lumen of inner member 420, 520. After fixation member 115 is engaged at the implant site, the operator may open valve member 286 to release tether 12, grasp the tether holder, and tug with tether 12 on device 1200 to test a holding force of the engaged of fixation member 115 or to disengage fixation member 115, if the operator has determined that it is necessary to reposition device 1200 at another implant site.

Figure 6A:
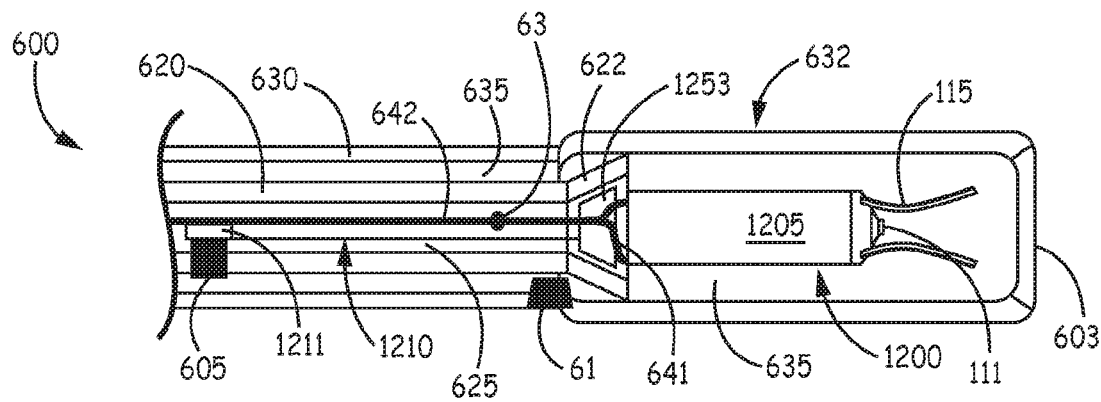
FIG. 6A is a cross-section view through a distal portion of yet another delivery tool employed by an interventional medical system, according to some embodiments.
Figure 6B:
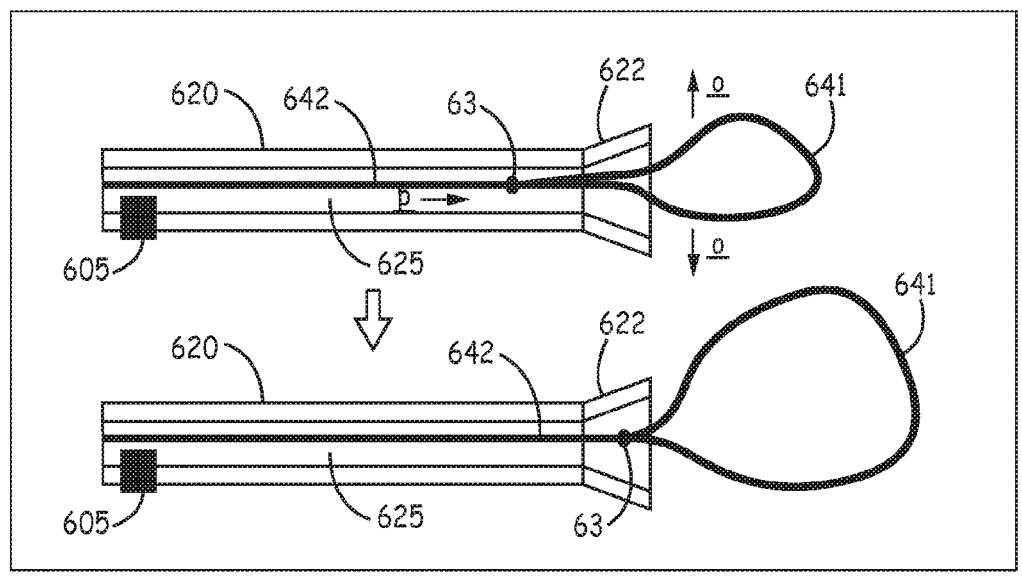
FIG. 6B is a schematic demonstrating an opening operation of a snare member of the tool shown in FIG. 6A, according to some methods of the present invention.

According to some alternate embodiments, rather than employing tether 12, interventional medical systems of the present invention may employ a snare member, for example, as illustrated in FIGS. 6A-B. FIG. 6A is a cross-section view through a distal portion of yet another delivery tool 600; and FIG. 6B is a schematic demonstrating an opening operation of a snare member of tool 600, according to some methods of the present invention. FIG. 6A illustrates tool 600, like tools 400, 500, including an inner member 620 and a deployment tube 630, wherein inner member 620 extends within a lumen 635 of tube 630 such that tube 630 is movable with respect to inner member 620, as described above for tools 400, 500, for example, via a control member of a handle of tool 600, for example, control member 212 of handle 210 (FIGS. 3A-B). Also like tools 400, 500, FIG. 6A shows device 1200 contained in a distal-most portion 632 of tube 630 with device housing 1205 abutting a distal end 622 of inner member 620, and with device extension 1210, extending within a lumen 625 of inner member 620 such that sense electrode 1211 interfaces with an inner conductive feature 605 of inner member 620. FIG. 6A further illustrates the snare member of delivery tool 600 including an elongate shaft 642 and a loop 641 coupled to a distal end of shaft 642 at a junction 63. Snare member shaft 642 extends alongside extension 1210 within lumen 625 of inner member 620, and loop 641 is closed around a snare attachment feature 1253 of device housing 1205 (feature 1253 also seen in FIG. 2A), when junction 63 of the snare member is located within lumen 625, as shown in FIG. 6A, so that a majority of loop 641 is constrained within lumen 625.

According to the illustrated embodiment, the snare member is slideably engaged within lumen 625, but a proximal segment of shaft 642 may be secured against sliding by a valve member 286 of handle 210 (FIG. 3B) to keep loop 641 closed around feature 1253 of device 1200 while an operator navigates distal-most portion 632 of delivery tool 600, with device 1200 contained therein, to a target implant site (e.g., in the right ventricle RV), and while the operator retracts deployment tube 630 relative to inner member 620 and device 1200 and engages fixation member 115 of device 1200 at the target implant site by pushing on inner member 620. FIG. 6A further illustrates deployment tube 630 of delivery tool 600 including an outer conductive feature 61 located at a proximal end of distal-most portion 632, so that, when deployment tube 630 is retracted to expose device fixation member 115 for engagement with tissue at the target implant site, inner conductive feature 605 of inner member 620 comes into electrical contact with outer conductive feature 61 to provide a conductive pathway between sense electrode 1211, interfacing with inner conductive feature 605, and a location outside deployment tube 630, for example, the blood pool in the right ventricle RV. Thus, sensing via electrode 1211 may be evaluated, via the conductive pathway, without having to withdraw tool 600 from over an entirety of device 1200. According to some embodiments, as illustrated, inner and outer conductive features 605, 61 are formed by electrically conductive segments, for example, integrated into the walls of inner member 620 and deployment tube 630, respectfully, according to any of the embodiments described above. According to some alternate embodiments, inner and outer conductive features 605, 61 may be defined by apertures formed through a wall of inner member 620 and a wall of deployment tube 630, respectively, to provide fluid communication between sense electrode 1211 and the blood pool outside deployment tube 630, as described above for delivery tool 400.

Following the evaluation of sensing via electrode 1211, and if adequate sensing is confirmed, the operator may release device 1200 from the snare member. With reference to FIG. 6B, the snare member is released when the operator advances, or pushes shaft 642 of the snare member distally, per arrow p, to open snare loop 641, per arrows o. According to some methods, prior to releasing device 1200 from the snare member, the operator can test a holding force of the engaged fixation member 115 by applying a tug force to snare shaft 642; also, the operator can employ the snare member, with snare loop 641 closed around device attachment feature 1253, to disengage fixation member 115, if the operator has determined that it is necessary to reposition device 1200 at another implant site.

Figure 7C:
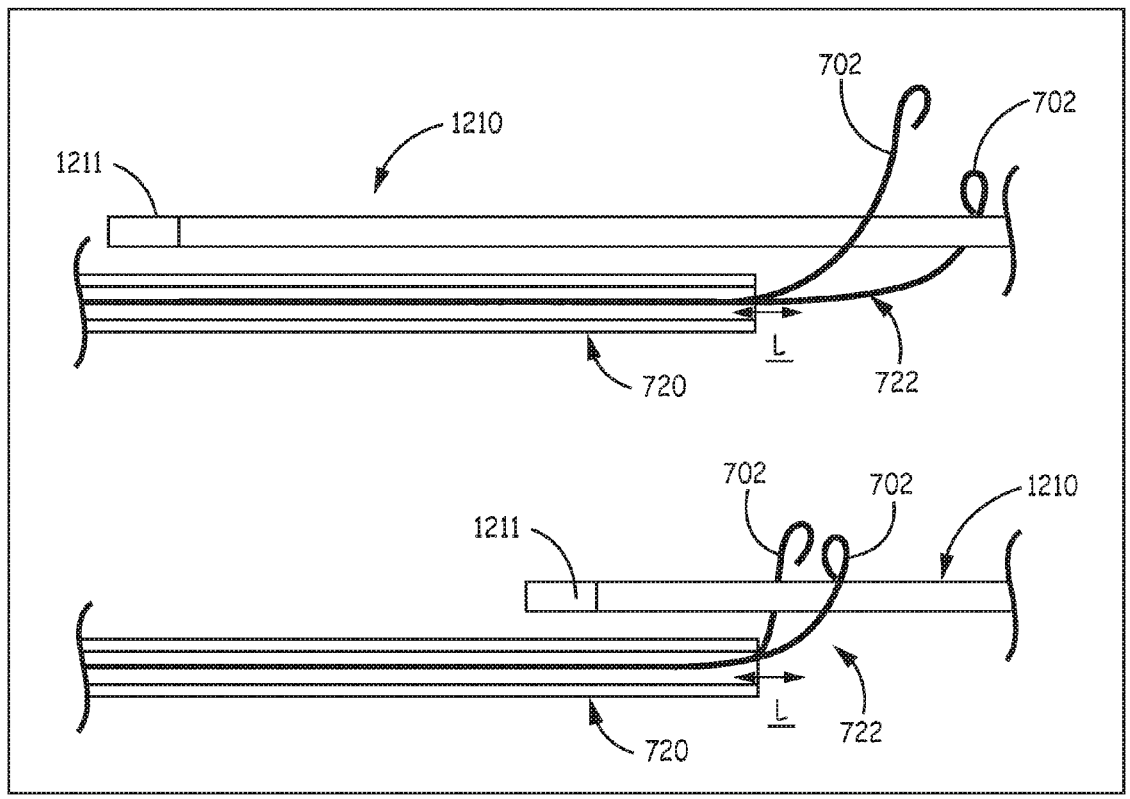
FIG. 7C is a schematic demonstrating operation of a grasping mechanism of the tool shown in FIGS. 7A-B, according to some methods of the present invention.

FIGS. 7A-B are partial cut-way section views of proximal and distal portions of an interventional medical system that includes a delivery tool 700, according to some additional embodiments. Tool 700, like tools 200, 400, 500, 600, includes an elongate deployment tube 730, wherein deployment tube 730 includes a proximal end coupled to a control member 712 of a handle 710, a distal-most portion 732, and a lumen 735 that extends from a proximal opening thereof at the proximal end to a distal opening 703 thereof, which terminates distal-most portion 732. FIGS. 7A-B illustrate tool 700 further including an elongate grasping mechanism formed by a tubular shaft 720 and a pair of arms 722 that are longitudinally moveable within a lumen of shaft 720, for example, as illustrated in the schematic of FIG. 7C. FIG. 7A further illustrates device 1200 loaded into tool 700 so that distal-most portion 732 of deployment tube 730 contains an entirety of device housing 1205 and fixation member 115, so that extension 1210 extends proximally from distal-most portion 732 within lumen 735 of deployment tube 730; curved distal ends 702 of grasping mechanism arms 722 that grip extension 1210 of device 1200 are also contained in distal-most portion 732. With further reference to FIG. 7A, an internal shoulder 731 of deployment tube 730 is located at a proximal end of distal-most portion 732, and, according to some embodiments, abuts curved distal ends 702 of grasping mechanism arms 722.

With further reference to FIGS. 7A-B, the grasping mechanism extends within lumen 735 of deployment tube 730 such that an entirety of deployment tube 730 is longitudinally moveable with respect to the grasping mechanism by means of control member 712. Thus, after navigating distal-most portion 735 of tool 700 into proximity with a target implant site in a patient's venous system, for example, in the right ventricle RV (FIG. 2B), an operator can move control member 712, per arrow B (FIG. 7A), to retract deployment tube 730, per arrow W (FIG. 7B), with respect to the gripped device 1200, and expose device fixation member 115 out through distal opening 703 of lumen 735, thereby engaging the exposed fixation member 115 with tissue T at the target implant site. According to some methods, the operator can simultaneously, or subsequently, apply a modest push force to device 1200, through the grasping mechanism, to help engage the exposed fixation member 115. Alternately, or in addition, after fixation member 115 is engaged, the operator may employ the grasping mechanism, while arms 722 thereof grip device extension 1210, to apply a tug force that tests a holding force of fixation member 115 and/or disengages fixation member 115, according to some methods.

FIGS. 7A-B further illustrate tool 700 including an optional conductive feature 71 formed in deployment tube 730, so that, when electrode 1211 is approximately aligned with feature 71, for example, as illustrated in FIG. 7B, a conductive pathway C is formed between electrode 1211 and the blood pool outside tool 700 to allow the operator to evaluate sensing of sense electrode 1211 without having to withdraw tool 700 from over an entirety of device 1200. Like the conductive features described above for tools 400, 500, 600, optional conductive feature 71 may be defined by one or more apertures providing fluid communication between the blood pool and the aligned sense electrode 1211; alternately, optional conductive feature 71 may be defined by an electrically conductive segment of deployment tube 730, which is configured to make electrical contact with the aligned sense electrode 1211. Any of the above described exemplary embodiments of conductive segments may be employed in deployment tube 730.

FIG. 7A shows a proximal end the grasping mechanism extending proximally from handle 710, according to some embodiments, to provide the operator with access for the manipulation/operation of the grasping mechanism. FIG. 7C is a schematic demonstrating operation of the grasping mechanism, according to some methods of the present invention. As described above, grasping mechanism arms 722 are longitudinally moveable within the lumen of tubular shaft 720, per double-headed arrow L, so that the operator may advance arms 722 within shaft 720 to spread curved distal ends 702 of arms 722 apart from one another (upper part of FIG. 7C schematic), thereby releasing a grip on device extension 1210, and may withdraw arms 722 within shaft to bring curved distal ends 702 together (lower part of FIG. 7C schematic), thereby gripping device extension 1210. With reference back to FIGS. 2A-B, deployment tool 700 may be particularly suited to accommodate a longer length of extension 1210, in which distance X is between approximately 10 cm and approximately 15 cm, so that the operator can locate electrode 1211 at a desired location in the right atrium RA, for example as illustrated in FIG. 8.

Figure 8:
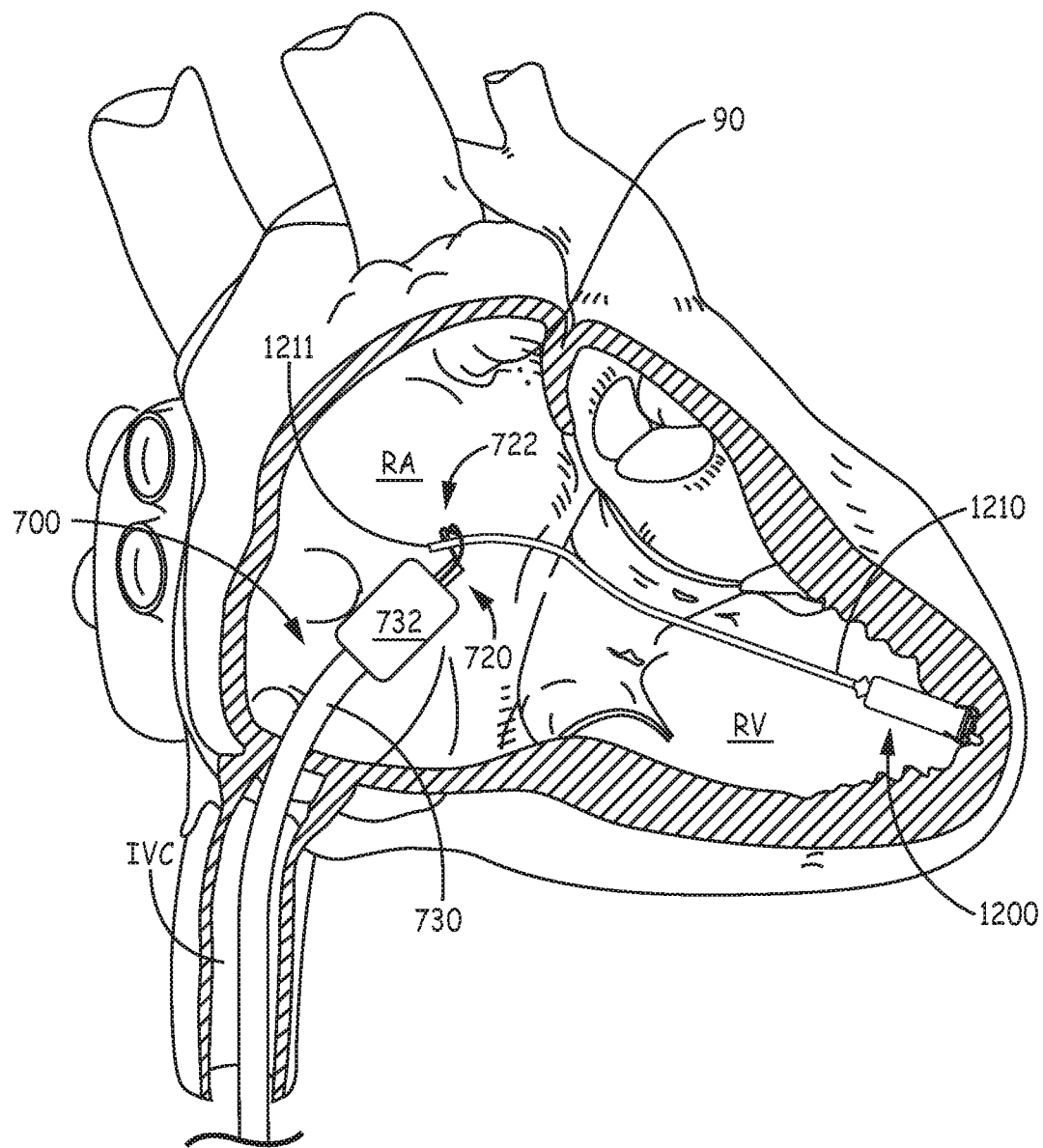
FIG. 8 is a schematic showing the exemplary implanted device together with the tool of FIGS. 7A-C located and positioned to move an extension of the device to a desired location.

FIG. 8 is a schematic showing the implanted device 1200, which has the longer extension, after tool 700 has been withdrawn into the right atrium RA. According to some methods, after the operator engages fixation member 115 of device 1200, for example, as described above, the operator withdraws tool 700, relative to the implanted device 1200 and the grasping mechanism, until tool 700 is located in the right atrium RA; then, by spreading arm distal ends 702 of the grasping mechanism apart (e.g., per the upper part of FIG. 7C), the operator may move the grasping mechanism proximally along a length of extension 1210 until the grasping mechanism is located in the right atrium RA, for example, in proximity to distal opening 703 of deployment tube 730, as shown in FIG. 8. When located within the right atrium RA, the grasping mechanism may be manipulated by the operator so that arms 722 grip around extension 1210 (e.g., per the lower part of FIG. 7C schematic); then, the operator can further manipulate the grasping mechanism to position a distal end of extension 1210 at the desired location in the right atrium RA, for example, by alternately spreading apart and closing together arms 722 around extension 1210, while moving the grasping mechanism relative to deployment tube 730.

Figure 9:
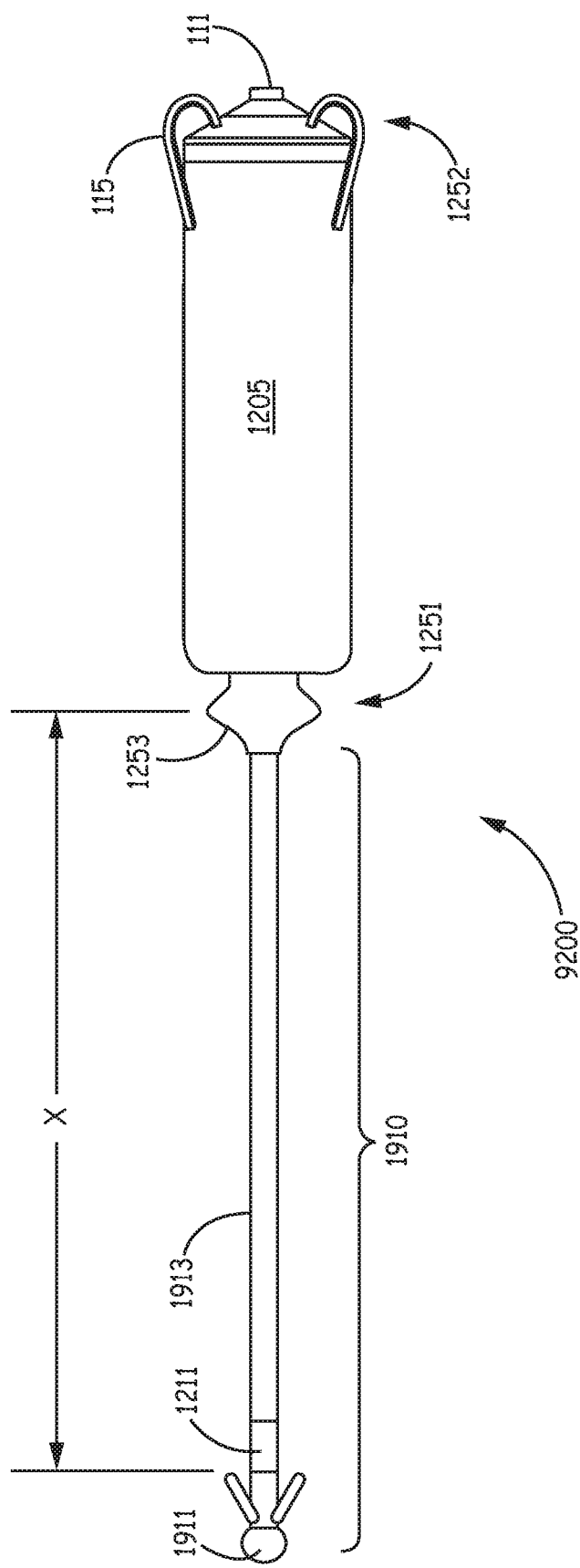
FIG. 9 is a plan view of an alternate embodiment of an exemplary implantable medical device, which may be employed by systems of the present invention.

According to some methods, if the operator deploys a dual chamber device 1900, an example of which is illustrated in FIG. 9, with delivery tool 700, in lieu of device 1200, the grasping mechanism can be employed by the operator to position a pace-sense pair of electrodes 1911, 1211 in a right atrial appendage 90 (FIG. 8), after engaging fixation member 115 with tissue T in the right ventricle RV, as described above. FIG. 9 shows pace electrode 1911 terminating a distal end of an extension 1910 of device 1900, with sense electrode 1211 spaced proximally therefrom. Extension 1910, like extension 1210 of device 200, extends proximally from proximal end 1251 of device housing 1205, such that pace-sense pair of electrodes 1911, 1211 is spaced a distance x from proximal end 1251 of housing 1205, wherein distance x may be between approximately 10 cm and approximately 15 cm. According to the illustrated embodiment, extension 1910 includes a pair of insulated conductors 1913, for example, a coiled medical grade stainless steel or MP35N wires isolated from one another and disposed within a medical grade silicone or polyurethane jacket, one of which electrically couples sense electrode 1211 to device housing 1205, for example, via a crimp or a weld, and the other of which couples pace electrode 1911 to the aforementioned electronic controller contained within housing 1205, via a hermetic feedthrough assembly like those known to those skilled in the art of implantable medical devices. A fixation member, for example, the illustrated tine assembly, similar to that known in the art, may be coupled to extension 1910 in proximity to electrode 1911 to hold electrode 1911 in intimate tissue contact within atrial appendage 90.

With reference back to FIGS. 7A-C, the larger curvature of curved distal ends 702 of arms 722 gives the grasping mechanism a canted tip to facilitate steering of the gripped extension 1210 to the desired location. According to an exemplary embodiment, arms 722 are formed from 0.015 inch to 0.030 inch diameter stainless steel wire, and tubular shaft 720 has an approximate diameter of 4 to 6 French (0.052 inch to 0.078 inch) and is formed from a braid reinforced polymer, according to any suitable construction known in the art of interventional cardiology.

In the foregoing detailed description, the invention has been described with reference to specific embodiments. However, it may be appreciated that various modifications and changes can be made without departing from the scope of the invention as set forth in the appended claims.

The invention claimed is:

1. A delivery tool facilitating deployment of an implantable medical device, the device including an electronic controller, a hermetically sealed housing containing the controller, a fixation member, and an extension coupled to the controller, the extension extending from a proximal end of the housing, the extension including a sense electrode, and the tool comprising:
 a handle including a control member;
 an elongate grasping mechanism including a tubular shaft and a pair of arms longitudinally movable within a lumen of the tubular shaft, each arm including a curved distal end protruding from a distal opening of the lumen of the shaft, at a distal end of the shaft, the curved distal ends being configured to spread apart from one another and to close together, via longitudinal movement of the arms within the lumen of the shaft, and the curved distal ends being configured to grip the extension of the device; and
 an elongate deployment tube including a proximal end coupled to the control member of the handle, a distal-most portion, and a lumen extending from a proximal opening thereof at the proximal end of the deployment tube to a distal opening thereof that terminates the distal-most portion at a distal end thereof, the grasping mechanism extending within the lumen of the deployment tube such that an entirety of the deployment tube is longitudinally moveable with respect to the grasping mechanism by means of the control member of the handle,
 wherein the lumen of the deployment tube, along a length of the distal-most portion, is sized to contain an entirety of the housing of the device and the fixation member together with the curved distal ends of the arms of the grasping mechanism gripping the extension of the device when the extension of the device extends proximally from the distal-most portion within the lumen of the deployment tube,
 wherein a diameter of the lumen of the deployment tube along the length of the distal-most portion is greater than the diameter of the lumen of the deployment tube proximal of the distal-most portion, and
 wherein the grasping mechanism is moveable outside the lumen of the deployment tube, distal to the distal opening thereof.

2. The tool of claim 1, wherein the deployment tube further includes an internal shoulder located at a proximal end of the distal-most portion, the shoulder configured to abut the curved distal ends of the arms of the grasping mechanism.

3. The tool of claim 1, wherein the deployment tube further includes a conductive feature located proximal to, and in proximity to the distal-most portion thereof, the conductive feature being configured to provide a conductive pathway between the sense electrode of the extension of the device and a location outside the deployment tube, when the sense electrode is aligned with the conductive feature via movement of the deployment tube with respect to the device.

4. The tool of claim 3, wherein the conductive feature comprises one or more apertures providing fluid communication between the location outside the deployment tube and the aligned sense electrode of the extension of the device.

5. The tool of claim 3, wherein the conductive feature comprises a conductive segment of the deployment tube being in electrical contact with the aligned sense electrode of the extension of the device.

6. The tool of claim 5, wherein the conductive segment comprises a conductive material dispersed within a wall of the deployment tube.

7. The tool of claim 5, wherein the conductive segment comprises a conductive insert joined to a wall of the deployment tube.

8. A delivery tool facilitating deployment of an implantable medical device, the device including an electronic controller, a hermetically sealed housing containing the controller, a fixation member, and an extension coupled to the controller, the extension extending from a proximal end of the housing, the extension including a sense electrode, and the tool comprising:
 a handle including a control member;
 an elongate grasping mechanism including a tubular shaft and a pair of arms longitudinally movable within a lumen of the tubular shaft, each arm including a curved distal end protruding from a distal opening of the lumen of the shaft, at a distal end of the shaft, the curved distal ends being configured to spread apart from one another and to close together, via longitudinal movement of the arms within the lumen of the shaft, and the curved distal ends being configured to grip the extension of the device; and an elongate deployment tube including a proximal end coupled to the control member of the handle, a distal-most portion, and a lumen extending from a proximal opening thereof at the proximal end of the deployment tube to a distal opening thereof that terminates the distal-most portion at a distal end thereof, the grasping mechanism extending within the lumen of the deployment tube such that an entirety of the deployment tube is longitudinally moveable with respect to the grasping mechanism by means of the control member of the handle, wherein the lumen of the deployment tube, along a length of the distal-most portion, is sized to contain an entirety of the housing of the device and the fixation member together with the curved distal ends of the arms of the grasping mechanism gripping the extension of the device when the extension of the device extends proximally from the distal-most portion within the lumen of the deployment tube, wherein, within the lumen of the deployment tube, the tubular shaft of the grasping mechanism is configured to extend alongside the extension of the device, wherein the tubular shaft of the grasping mechanism is configured to extend along a first longitudinal axis and the extension of the device is configured to extend along a second longitudinal axis offset from the first longitudinal axis, and wherein the grasping mechanism is moveable outside the lumen of the deployment tube, distal to the distal opening thereof.

9. The tool of claim 8, wherein the deployment tube further includes an internal shoulder located at a proximal end of the distal-most portion, the shoulder configured to abut the curved distal ends of the arms of the grasping mechanism.

10. The tool of claim 8, wherein the deployment tube further includes a conductive feature located proximal to, and in proximity to the distal-most portion thereof, the conductive feature being configured to provide a conductive pathway between the sense electrode of the extension of the device and a location outside the deployment tube, when the sense electrode is aligned with the conductive feature via movement of the deployment tube with respect to the device.

11. The tool of claim 10, wherein the conductive feature comprises one or more apertures providing fluid communication between the location outside the deployment tube and the aligned sense electrode of the extension of the device.

12. The tool of claim 10, wherein the conductive feature comprises a conductive segment of the deployment tube being in electrical contact with the aligned sense electrode of the extension of the device.

13. The tool of claim 12, wherein the conductive segment comprises a conductive material dispersed within a wall of the deployment tube.

14. The tool of claim 12, wherein the conductive segment comprises a conductive insert joined to a wall of the deployment tube.

* * * * *